(12) United States Patent
Jeon et al.

(10) Patent No.: US 11,452,594 B2
(45) Date of Patent: Sep. 27, 2022

(54) INTRAOCULAR LENS AND METHOD OF MANUFACTURING THE SAME

(71) Applicant: KOREA INSTITUTE OF SCIENCE AND TECHNOLOGY, Seoul (KR)

(72) Inventors: Hojeong Jeon, Seoul (KR); Myoung-Ryul Ok, Seoul (KR); Yu Chan Kim, Seoul (KR); Hyun Kwang Seok, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/836,925

(22) Filed: Apr. 1, 2020

(65) Prior Publication Data
US 2020/0345479 A1  Nov. 5, 2020

(30) Foreign Application Priority Data

May 2, 2019  (KR) .................. 10-2019-0051471

(51) Int. Cl.
*A61F 2/16* (2006.01)
*A61F 2/00* (2006.01)

(52) U.S. Cl.
CPC ........ *A61F 2/16* (2013.01); *A61F 2002/0081* (2013.01); *A61F 2002/1689* (2013.01); *A61F 2240/002* (2013.01)

(58) Field of Classification Search
CPC ........ A61F 2/16; A61F 2/1613; A61F 2/0077; A61F 2002/1696; A61F 2002/1681–16903; A61F 2002/0081
See application file for complete search history.

(56) References Cited

U.S. PATENT DOCUMENTS 5,693,094 A * 12/1997 Young .................. A61F 2/16
                                                              128/898
2012/0259411 A1* 10/2012 Hong ................... G02C 7/049
                                                              351/159.01
(Continued)

FOREIGN PATENT DOCUMENTS

JP        2014522251 A     9/2014
KR   1020010018345 A     3/2001
(Continued)

OTHER PUBLICATIONS

International Search Report dated Jun. 8, 2020 for PCT/KR2020/002688. In conformance with MPEP 609—Concise explanation of the relevance includes issue date of a foreign OA and references cited therein.

*Primary Examiner* — Jennifer Dieterle
*Assistant Examiner* — Tiffany P Shipmon
(74) *Attorney, Agent, or Firm* — Cantor Colburn LLP

(57) ABSTRACT

Provided is an intraocular lens including: an optic portion; and a haptic portion extending from the optic portion, wherein a pattern having ridges and grooves is formed on at least one of the optic portion and the haptic portion, and each of the grooves has a nanostructure roughness. Provided also is a method of manufacturing an intraocular lens, the method including: seating an object to be processed including an optic portion and at least one haptic portion extending from the optic portion, processing a predetermined pattern for guiding cells by performing laser irradiation on the haptic portion and the optic portion, forming grooves having a nanostructure surface roughness in the predetermined pattern formed by laser beams, and the surface of each of the grooves has an average roughness Ra less than 200 nm.

11 Claims, 15 Drawing Sheets

(56) References Cited

U.S. PATENT DOCUMENTS

2016/0095698 A1* 4/2016 Jeon .................... A61F 2/16
                                                           623/6.43
2017/0189168 A1* 7/2017 Zickler ............... H04W 52/146

FOREIGN PATENT DOCUMENTS

| KR | 1020110083672 A | 7/2011 |
| KR | 1020160040807 A | 4/2016 |
| KR | 1020170036056 A | 3/2017 |

* cited by examiner

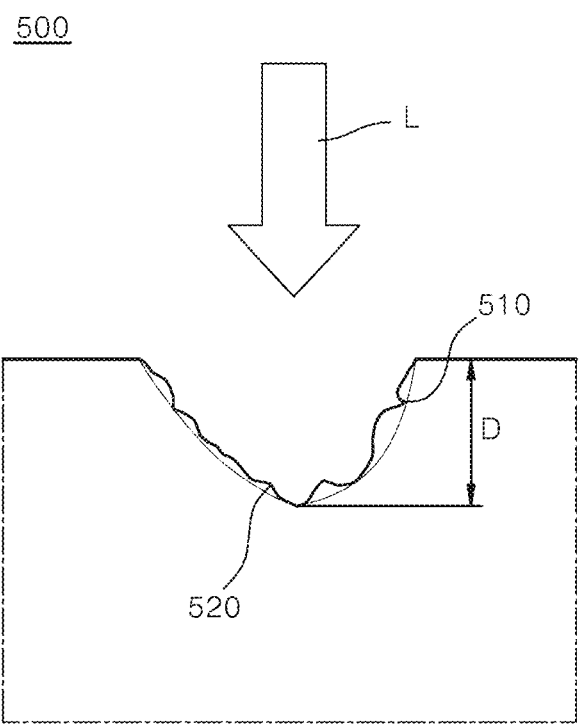

INTRAOCULAR LENS AND METHOD OF MANUFACTURING THE SAME

CROSS-REFERENCE TO RELATED APPLICATION

This application claims the benefit of Korean Patent Application No. 10-2019-0051471, filed on May 2, 2019, in the Korean Intellectual Property Office, the disclosure of which is incorporated herein in its entirety by reference.

BACKGROUND

1. Field

The present invention relates to an intraocular lens and a method of manufacturing the same.

2. Description of the Related Art

In general, a human eye is similar to a camera in terms of structure and function. An eye lens having a convex lens-shaped transparent structure is provided behind a pupil to function as a camera lens.

When the eye lens becomes opaque due to damage from the outside or factors such as unnecessary abuse of eye drops, radiographic exposure, or exposure to various harmful electromagnetic waves, a cataract may be caused. As one of the surgical methods for treating the cataract, a method of implanting an intraocular lens capable of replacing the function of the lens has been used.

In this case, most surgical operations have been made to insert the intraocular lens into the inside of a part of an eyeball called a capsular bag or into a space between the capsular bag and an iris.

However, a relapse of opacity is likely to occur by proliferation of cells leading to an after cataract and migration of cells to the intraocular lens, even after an operation. Therefore, there is a need to develop a technique capable of delaying or inhibiting the proliferation and migration of cells and the like that induce the after cataract.

RELATED ART

Patent Documents

Patent Document 1: Korean Laid-open Patent Application No. 2001-0018345 (Mar. 5, 2001)

SUMMARY

An object of the present invention is to provide an intraocular lens preventing relapse of eye diseases such as after cataract by controlling the behavior of cells (e.g., epithelial cells) passing through a particular pattern by forming the pattern having a predetermine width or the like on the intraocular lens.

Another object of the present invention is to provide an intraocular lens controlling the behavior of cells using nanostructure surface roughness in a particular pattern formed to have a predetermine width or the like on the intraocular lens.

Another object of the present invention is to provide an intraocular lens capable of guiding cells to migrate in one direction by forming a boundary portion inhibiting the migration of the cells in a pattern formed on the intraocular lens.

Additional aspects will be set forth in part in the description which follows and, in part, will be apparent from the description, or may be learned by practice of the presented embodiments.

According to an aspect of the present invention to achieve the object, provided is an intraocular lens including: an optic portion; and a haptic portion extending from the optic portion, wherein a pattern having ridges and grooves is formed on at least one of the optic portion and the haptic portion, and each of the grooves has a nanostructure roughness.

The surface of the groove may have an average roughness Ra less than 200 nm.

The surface of the groove may have an average roughness Ra of 140 nm.

The ridges, the grooves, or both of the rides and grooves may include at least one ridge and/or groove having a different width.

The grooves may be formed to have a width of 10 μm.

The ridges may be formed to have a width of 5 μm.

A ratio between a width of each ridge and a width of each groove may be in the range of 1:2 to 1:8.

The pattern may be formed over the haptic portion and the optic portion, the ridges may be formed to have a width of 5 μm and the grooves are formed to have different widths according to sections, and a width of a groove formed on the haptic portion may be greater than a width of a groove formed on the optic portion.

The pattern may be formed over front and rear surfaces of the optic portion and front and rear surfaces of the haptic portion.

The pattern may be formed on at least one of the front and rear surfaces of at least one of the optic portion and the haptic portion.

The pattern may be continuously formed over the front and rear surfaces via a side surface.

Each of the grooves may include a boundary portion configured to delay or inhibit migration of cells.

The boundary portion may include a plurality of cell migration paths formed within a width of the groove to change a migration speed of the cells.

The boundary portion may obliquely extend inward from side walls of the groove to guide a migration direction of cells by narrowing a cross-sectional area through which cells pass in a forward direction of cell migration and blocking the cell migration in a backward direction.

The boundary portion may be formed to protrude upward from the bottom surface of the groove and obliquely extend to bypass and block migration of cells in a forward direction where the cells move and enlarge a cross-sectional area through which the cells pass in a backward direction.

According to another aspect of the present invention, provided is a method of manufacturing an intraocular lens including: seating an object to be processed including an optic portion and at least one haptic portion extending from the optic portion, processing a predetermined pattern for guiding cells by performing laser irradiation on the haptic portion and the optic portion, forming grooves having a nanostructure surface roughness in the predetermined pattern formed by laser beams, and the surface of each of the grooves has an average roughness Ra less than 200 nm.

BRIEF DESCRIPTION OF THE DRAWINGS

These and/or other aspects will become apparent and more readily appreciated from the following description of the embodiments, taken in conjunction with the accompanying drawings in which:

FIG. 3 is a cross-sectional view of a pattern according to an embodiment of the present invention;

DETAILED DESCRIPTION

Hereinafter, embodiments of the present invention will be described in detail with reference to the accompanying drawings. However, the embodiments are described by way of examples only and the present invention is not limited thereto.

In describing the present invention, when a detailed description of well-known technology relating to the present invention may unnecessarily make unclear the spirit of the present invention, a detailed description thereof will be omitted. Further, the following terminologies are defined in consideration of the functions in the present invention and may be construed in different ways by the intention of users and operators. Therefore, the definitions thereof should be construed based on the contents throughout the specification.

As a result, the spirit of the present invention is determined by the claims and the following embodiments may be provided to efficiently describe the spirit of the present invention to those skilled in the art.

Figure 1:
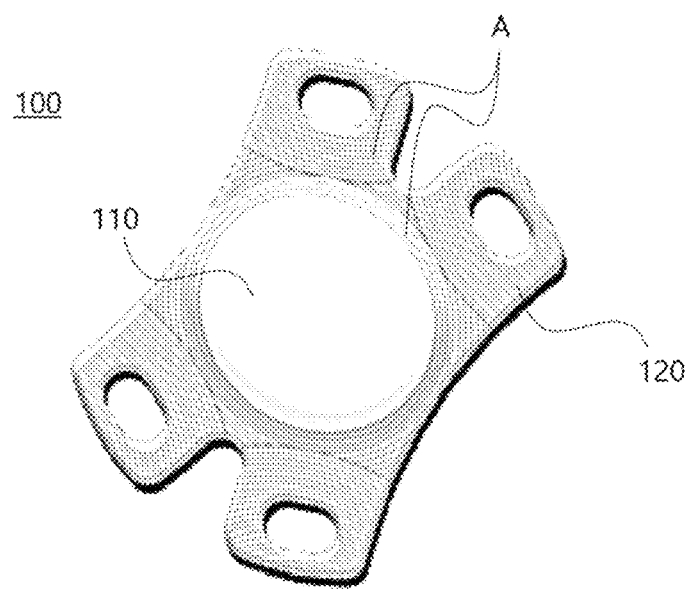
FIG. 1 is a diagram illustrating an intraocular lens according to an embodiment of the present invention.
Figure 2A:
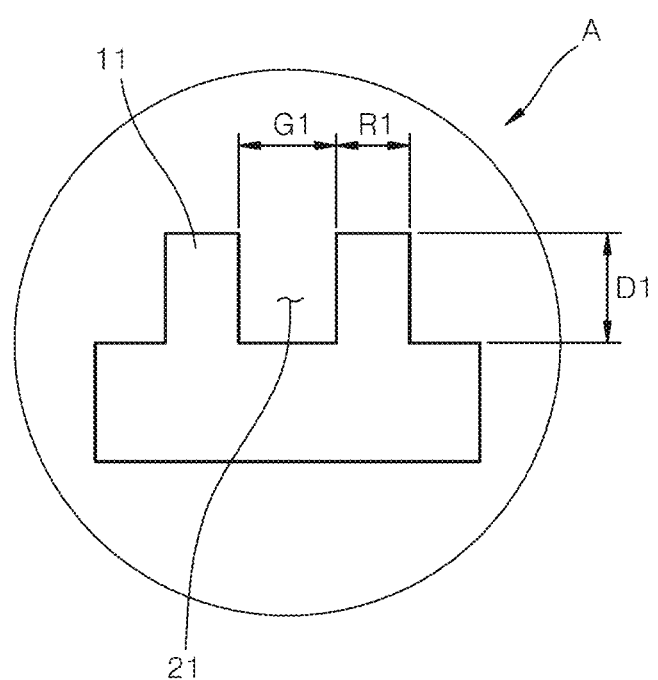
FIGS. 2A and 2B are cross-sectional views of patterns according to an embodiment of the present invention.
Figure 2B:
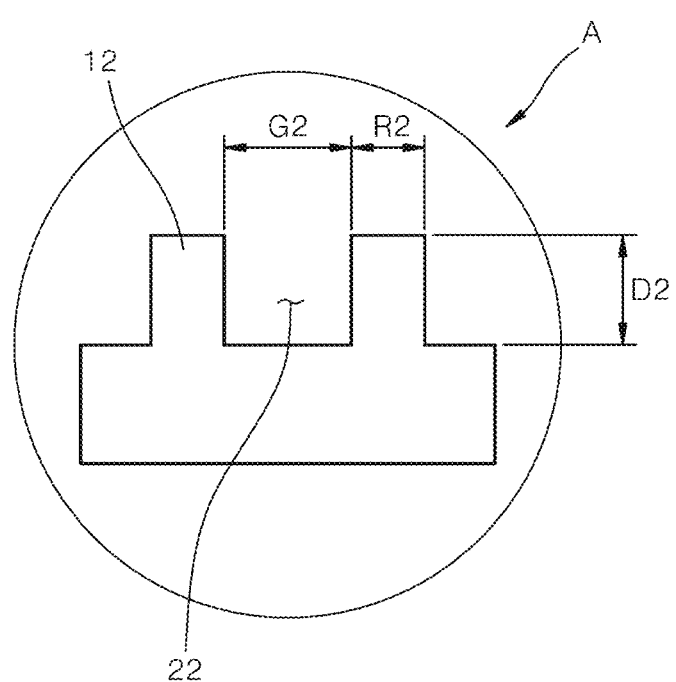

In intraocular lenses 100 and 300 shown in FIGS. 1, 2A, and 2B, portions having patterns are indicated by lines which are also applied to the following descriptions of the intraocular lenses 100 and 300.

In addition, a pattern A for describing the present invention may be formed on at least an optic portion 110 or 310 and may also be provided over a haptic portion 120 or 320. Meanwhile, the pattern A may also be formed on the haptic portion 120 or 320. Functions of each pattern A on the intraocular lenses 100 and 300 will be described in detail below.

FIG. 1 is a diagram illustrating an intraocular lens 100 according to an embodiment of the present invention.

Referring to FIG. 1, the intraocular lens 100 may include an optic portion 110 and a haptic portion 120. A pattern A may be formed on the optic portion 110 and the haptic portion 120. The pattern A may provide information on sizes of ridges 11 and 12 (FIGS. 2A and 2B) and grooves 21 and 22 (FIGS. 2A and 2B).

Specifically, the size information may include depths D1 and D2 (FIGS. 2A and 2B) and widths G1 and G2 (FIGS. 2A and 2B) of the grooves and depths D1 and D2 (FIGS. 2A and 2B) and widths R1 and R2 (FIGS. 2A and 2B) of the ridges. This size information may be described below with reference to FIGS. 2A and 2B. Meanwhile, when the optic portion 110 capable of transmitting light and having a circular shape in one portion thereof is implanted into a human body, the optic portion 110 may be provided to prevent foreign matters from being located on the optic portion 110 since light is incident on the optic portion 110. In this regard, the foreign matters may be epithelial cells that may cause eye disease such as after cataract. For example, the optic portion 110 may be implanted into a cataract patient after removing an opaque eye lens therefrom.

After the implantation, the intraocular lens may become opaque again by a small amount of ocular epithelial cells remaining in the human body and causing the after cataract. In order to prevent this, an intraocular lens 100, which is processed to have a pattern to delay or inhibit migration or proliferation of cells on the surface of the intraocular lens 100, may be implanted.

The intraocular lens 100 according to an embodiment of the present invention may be provided with the pattern A from an outer perimeter portion of the optic portion 110 to the haptic portion 120 as shown in FIG. 1. The outer perimeter portion refers to a range extending from an outer circumferential edge of the optic portion 110 such that the cells move farther away from the center of the optic portion 110. The pattern A may not be formed on the optic portion 110 from the center of the optic portion 110 to a predetermined distance in the radial direction in an area of the intraocular lens 100 excluding the above-described outer perimeter portion.

The pattern A may guide the foreign matters (e.g., epithelial cells) to move farther away from the center of the optic portion 110 or inhibit proliferation of the cells, thereby preventing the cells from moving to the portion of the optic portion 110 transmitting light.

In addition, FIG. 2A is a cross-sectional view of the pattern A of the present embodiment. FIG. 2B is a cross-sectional view of another pattern B of the present embodiment.

Referring to FIGS. 2A and 2B, the patterns A and B may be located separately according to the positions such as the optic portion or the haptic portion. For example, the pattern A located on the optic portion 110 may be formed to be larger than the pattern B located on the haptic portion 120. More specifically, a width G1 of a groove included in the pattern A may be smaller than a width G2 of a groove included in the pattern B.

For example, the width G1 of the groove included in the pattern A may be in the range of 5 μm to 30 μm. As the width G1 of the groove increases within the range, the mobility of the cells may decrease, and as the width G1 of the groove decreases, the mobility of the cells may increase. However, in consideration of sizes of the cells, when the width G1 of the groove is less than sizes of the cells, the influence of the grooves on the mobility of the cells may decrease. More specifically, the width G1 of the groove included in the pattern A may be 10 μm, and the width G2 of the groove included in the pattern B may be 30 μm. As described above, the mobility of the cells may vary depending on the sizes of the patterns A and B, and the sizes of the patterns A and B may be modified to control desired behavior of the cells. The numerical values of the widths may be values determined based on test results of the mobility of the cells performed using a plurality of patterns formed in different widths under the same conditions.

FIG. 3 is a cross-sectional view of a pattern according to an embodiment of the present invention.

Referring to FIGS. 2A, 2B, and 3, when a laser beam is emitted in a laser irradiation direction L, processing grooves may be formed on an intraocular lens 500. While the grooves 21 and 22 are formed, ridges 11 and 12 may be formed on both sides thereof. That is, the grooves 21 and 22 may be formed to be open between the adjacent ridges 11 and 12 to have predetermined depths D1 and D2, respectively. The grooves 21 and 22 may be provided with processing projections 510 and 520 providing finer nano-structural surface roughness, which will be described below with reference to the drawings to be more intuitively shown in the following drawings.

Meanwhile, the grooves 21 and 22 may be formed on the intraocular lens 100 by laser irradiation in the laser irradiation direction L. Thus, the grooves 21 and 22 may be formed in an intaglio shape engraved to a predetermined depth, which may be formed in the shape of a groove, a non-through hole, a drain, or the like. In this regard, the predetermined depth may be determined according to laser irradiation conditions and a material of the intraocular lens 100. For example, the laser irradiation conditions may include laser power, laser frequency, laser spot size, and laser irradiation time.

Specifically, when the grooves 21 and 22 are formed to the predetermined depth by laser irradiation, a desired depth of the grooves 21 and 22 may not be obtained by performing the laser irradiation once. That is, as the laser power increases, the predetermined depth may be formed within a shorter time. Meanwhile, when the processing is performed using high-power laser beams by a small number of times of irradiation, thermal deformation may occur according to the material of the intraocular lens 100, and the risk of damage on the intraocular lens 100 by the laser beams may increase. It is also noted that the surfaces of the grooves 21 and 22 processed by the high-power laser beams may have a higher roughness than the surfaces of the grooves 21 and 22 processed using low-power laser beams by a large number of times.

In this regard, processing by laser irradiation twice or more means that a deeper groove is formed than a groove that may be formed by performing laser irradiation once. To this end, areas of the intraocular lens 100 subjected to the laser irradiation may overlap. As a method of performing laser irradiation onto the intraocular lens 100 by overlapping laser beams, a method of emitting two or more laser beams to a portion of the intraocular lens 100 at a time interval may be used. Meanwhile, a ratio of overlapping laser beams may be referred to as an overlap distance (or overlap ratio).

The spot size, frequency, scan interval, and scanning speed of the laser beam may be factors determining the overlap distance, and the predetermined width and depth of the groove may be determined by the overlap distance. For example, as a pulse rate (frequency) increases and an irradiation time decreases, the overlap distance may decrease. On the contrary, as the frequency decreases and the irradiation time increases, the overlap distance may increase. In this regard, an increase in the overlap distance means an increase in the amount of energy emitted from the laser beam and applied to a unit area indicating that the predetermined depth may be obtained by selectively adjusting the frequency and irradiation time of the laser beam. Also, the overlap distance may be modified by setting the layer spot side to be smaller than the predetermined width of the groove and adjusting the scan interval and the number of scanning in a direction perpendicular to the scanning direction, and thus the predetermined width of the groove may be achieved.

Therefore, the widths and depths of the grooves 21 and 22 formed by laser irradiation are factors that may be determined in consideration of conditions such as the material of the intraocular lens 100 and the laser power, laser frequency, laser spot size, scanning speed, and scanning interval. Thus, the grooves 21 and 22 and the processing projections 510 and 520 described in an embodiment of the present invention may also be determined according to the above-described conditions.

Figure 4:
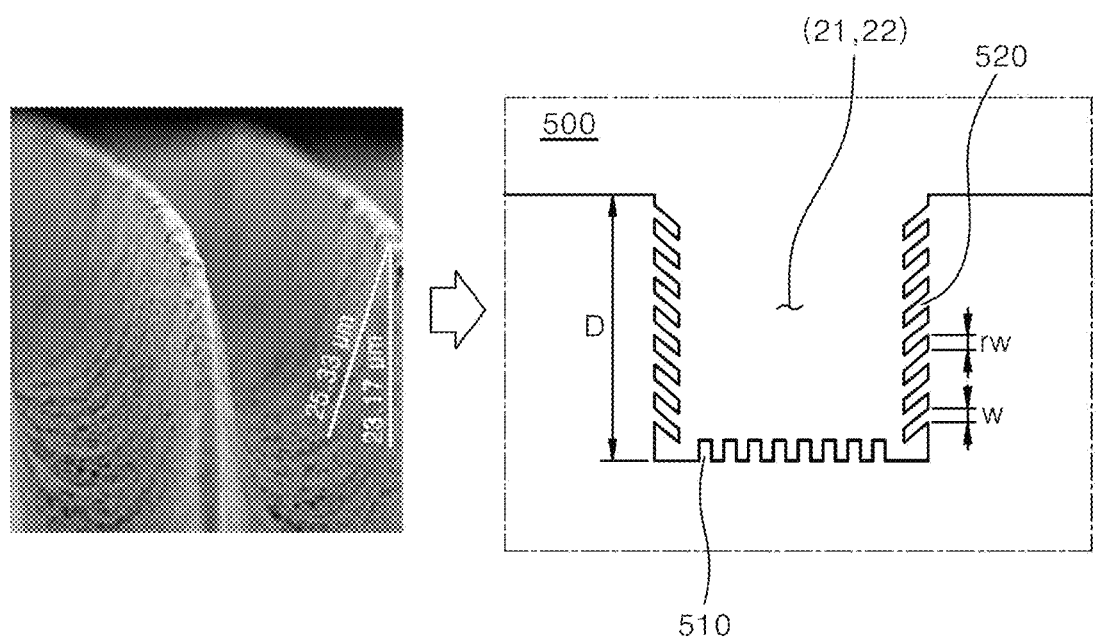
FIG. 4 shows a nano-sized structure formed on a groove according to an embodiment of the present invention.

FIG. 4 shows a nano-sized structure formed on the grooves 21 and 22 according to an embodiment of the present invention grooves 21 and 22.

Referring to FIG. 4, a nano-sized structure is formed on the surfaces of the grooves 21 and 22, and processing projections 510 and 520 may be formed thereon. The processing projections 510 and 520 may be formed to provide a nanostructure surface roughness and may be formed in a structure for delaying or inhibiting migration of cells.

A projection interval rw may be formed in the range of 0.1 μm to 10 μm. The projection interval rw is less than 0.1 μm, the roughness of the processing projections 510 and 520 decreases, and thereby deteriorating the ability to inhibit migration of the cells deteriorates. When the projection interval rw is greater than 10 μm, the number of the processing projections 510 and 520 decreases, thereby deteriorating the ability to inhibit migration of the cells. Thus, the projection interval rw may be formed in the range of 0.1 μm to 10 μm.

Also, a width w between adjacent processing projections 510 and 520 may be in the range of 0.1 μm to 10 μm. The width w is less than 0.1 μm, the length extending from the surfaces of the grooves 21 and 22 decreases, making it difficult to perform the function of inhibiting migration of the cells. When the width w is greater than 10 μm, the number of the processing projections 520 that may be provided in the processing groove 101 decreases, thereby making it difficult to secure a binding force. Thus, the width w of the projections may be in the range of 0.1 μm to 10 μm. Particularly, an optimum projection interval rw may be obtained based on results of experiments which will be described below with reference to FIGS. 6 to 9.

Figure 5:
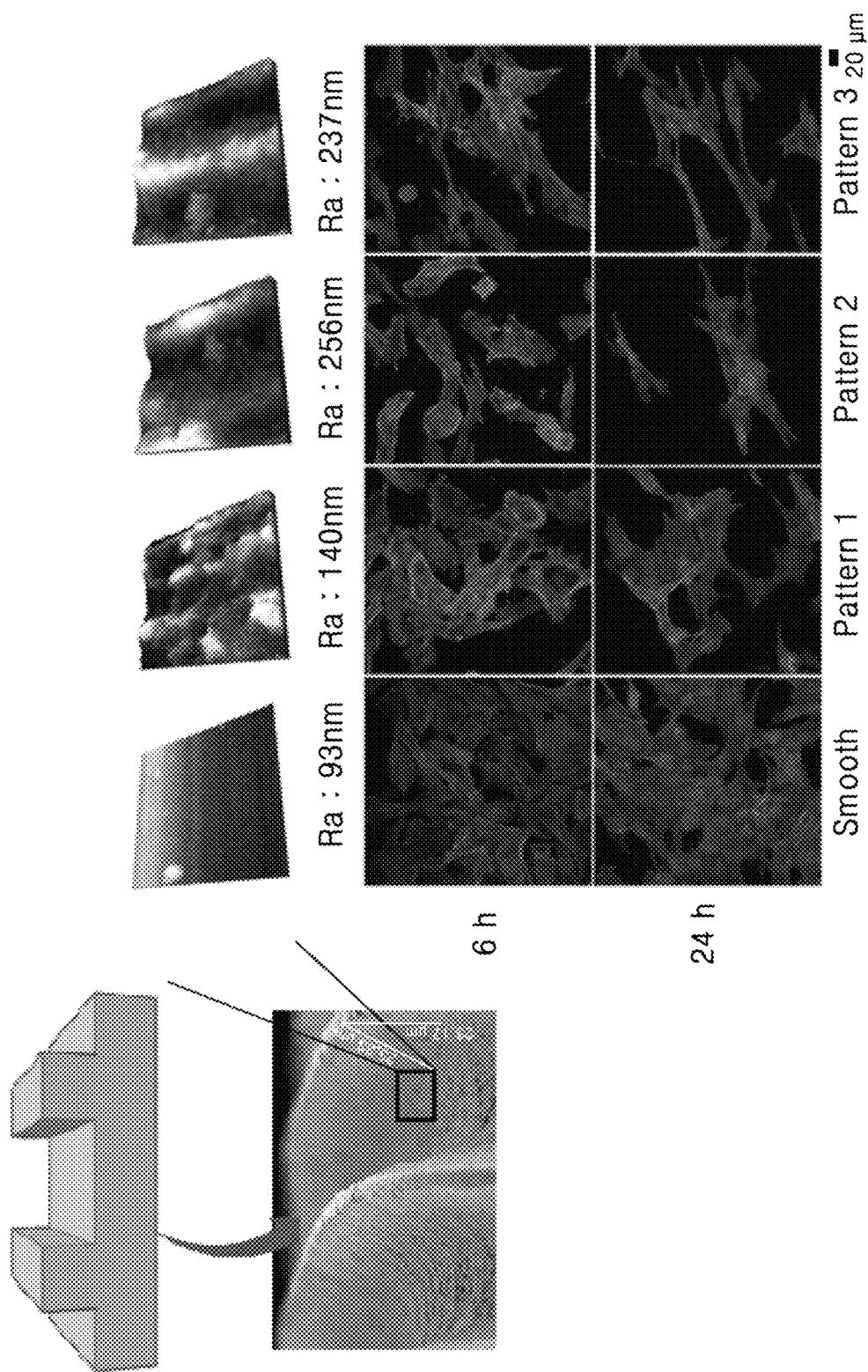
FIG. 5 shows surface roughnesses of surfaces of the grooves having various nano-sized structures formed according to femtosecond pulsed laser conditions.

FIG. 5 shows surface roughnesses of surfaces of the grooves 21 and 22 having various nano-sized structures formed according to femtosecond pulsed laser conditions.

Figure 6:
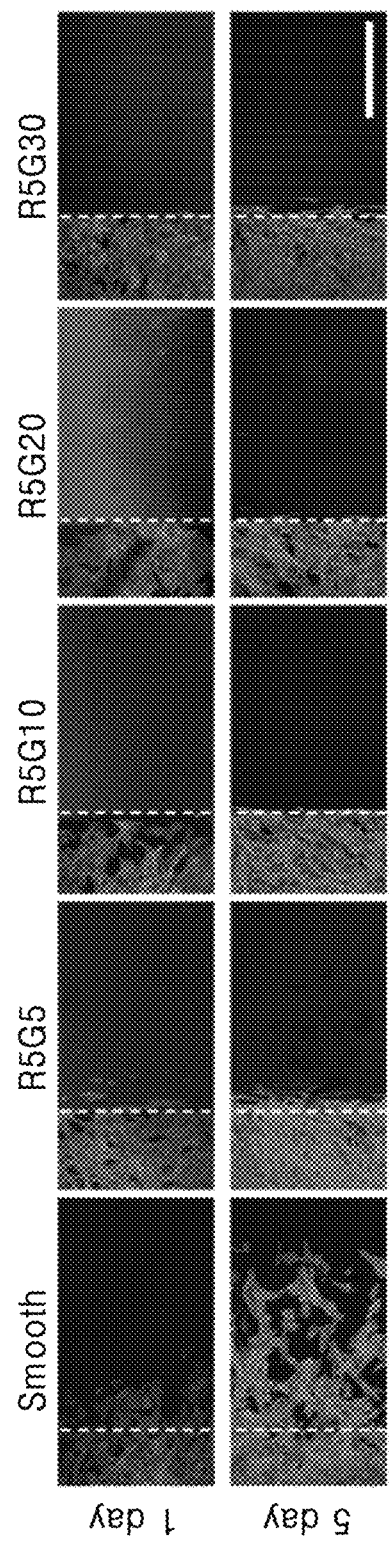
FIG. 6 shows microscope images of cells for identifying cell migration inhibiting rates in a direction traversing a pattern according to widths of grooves among sizes of the pattern according to embodiments of the present invention.

Referring to FIG. 5, when the surfaces of the grooves 21 and 22 were not treated with a laser, the surfaces may have an arithmetical average roughness (Ra) of 93 nm. In this regard, this Ra value indicates a surface that is not irradiated with laser beams to form ridges or grooves and may vary according to manufacturers or manufacturing processes of intraocular lenses. On the contrary, when laser irradiation was performed to form the ridges or grooves, surfaces having Ra values of 140 nm, 237 nm, and 256 nm may be obtained, respectively. The Ra value may vary according to the power and overlap distance of the laser beam. The overlap distance refers to an overlap distance in the X- or Y-axis direction, and the overlap distance in the X-axis direction may vary according to laser frequency, laser spot size, and scanning speed, and the overlap distance in the Y-axis direction may vary according to the spot size and scan interval. Referring to FIG. 6, in order to obtain surfaces having Ra values of 140 nm, 237 nm, and 256 nm, lasers beams having a spot size of 5 μm and laser powers (overlap distances) of 0.5 μJ (2.0 μm overlapping), 1.0 μJ (3.6 μm overlapping), and 2.0 μJ (4.7 μm overlapping) were used, respectively. However, in order to check chemical deformation on the surface of the material by laser processing, XPS analysis was performed to identify spectra of molecules constituting the surface. As a result, it was confirmed that chemical deformation did not occur even on the roughest surface having the Ra value of 256 nm.

As shown in FIG. 5, in order to identify the effects of nanostructures of the grooves 21 and 22 formed as described above on adhesion to the cells, cells were fixed and dyed in a concentration of $2.5*10^4/cm^2$ and the results were identified after cell observation time of 6 hours and 24 hours using a confocal microscope. As a result, as shown in FIG. 5, it was confirmed that cells grew more after 24 hours than 6 hours on the surface having the Ra value of 93 nm which was not treated with laser irradiation. Thus, it was confirmed that an increase in surface roughness by laser irradiation is advantages to prevent the migration of the cells.

In addition, as shown in FIG. 5, upon comparison of the Ra value of 140 nm (the former) with the Ra values of 256 nm and 237 nm (the latter) obtained by adjusting the laser power and overlap distance, it may be confirmed that cells are stretched in one direction in the latter case while the cells are not stretched in the former case. Specifically, as shown in FIG. 5, it was confirmed that adhesion of the cells to a surface having a surface roughness of 200 nm or more was significantly decreased. Although the cells were not stretched but remained in their original circular shapes on a surface having the surface roughness of 200 nm or more (Ra values of 256 nm and 237 nm) after 6 hours but stretched and had enlarged shapes after 24 hours.

Based on the results of FIG. 5, it is possible to adjust the surface roughness (Ra) to effectively inhibit migration of cells in term of the mobility of the cells. It may be understood that the surface having a surface roughness Ra value of 200 nm affects focal adhesion clusters of cells, thereby inhibiting the cells from being attached to the surface of the intraocular lens.

In order to identify whether epithelial cells moving along a posterior capsule are affected by the patterns A and B formed on the surface of the optic portion 210 or the haptic portion 220, the surface roughness may be set to have a Ra value of 140 nm for high adhesion of cells to the surface according to an embodiment of the present invention.

That is, preferably, the surface of the groove may have a surface roughness greater than a surface roughness of a state untreated with a laser (e.g., Ra value of 93 nm or more) and less than a surface roughness of a state treated with a laser to have high cell adhesion (e.g., Ra value less than 200 nm) as described above.

FIG. 6 shows microscope images of cells for identifying cell migration inhibiting rates in a direction traversing a pattern according to widths of grooves among sizes of the pattern according to embodiments of the present invention.

Referring to FIG. 6 indicating results of experiments on cell migration inhibition rate, the "smooth" on the left shows a migration result of a group of cultured cells on a plane untreated with a laser and three images on the right show migration results of cells in a direction traversing the ridges 11 and 12 and the grooves 21 and 22 included in the patterns A and B on surfaces having sequentially increased widths. In this regard, the widths R1 and R2 of the ridges were set to be equal to 5 μm (R5), and experimental groups, in which the widths G1 and G2 of the grooves (G5 to G30) were changed, were compared with each other.

While the above experimental groups are maintained for a certain period of time, the degree of cell migration may be identified. For example, a first row of FIG. 6 shows results of observing migration of the cells for 1 day (day 1), and a second row of FIG. 6 shows results of observing migration of the cells for 5 days (day 5) under the experimental conditions. As a result of examining the cell migration inhibition rates based on the present experiment, the highest cell migration inhibiting rate was obtained when the width of the grooves 21 and 22 was 10 μm. In one experiment, the cell migration inhibiting rate was 0% and the migration distance was 800 μm on the plane. When the width of the grooves 21 and 22 was 5 μm, the inhibition rate was 87.5% and the migration distance was 100 μm. When the width of the grooves 21 and 22 was 10 μm, the inhibition rate was 98.75% and the migration distance was 10 μm. When the width of the grooves 21 and 22 was 20 μm, the inhibition rate was 97.5% and the migration distance was 20 μm. When the width of the grooves 21 and 22 was 30 μm, the inhibition rate was 96.25% and the migration distance was 30 μm. These results are shown in the following table.

| object | migration distance on day 5 | cell migration inhibiting rate (1) |
| --- | --- | --- |
| Smooth | 800 μm | 0% |
| R5G5 | 100 μm | 87.5% |
| R5G10 | 10 μm | 98.75% |
| R5G20 | 20 μm | 97.5% |
| R5G30 | 30 μm | 96.25% |
| R20G10 | 60 μm | 92.5% |

(1) $$\text{cell migration inhibiting rate} = \frac{\left(\begin{array}{l}\text{migration distance on smooth surface} - \\ \text{migration distance on pattern surface}\end{array}\right)}{\text{migration distance on smooth surface}} \times 100$$

It was observed that all patterns exhibit superior effects on cell migration inhibition when compared to the cells stretched by about 1 mm on the surface without a pattern. More specifically, slight cell migration was observed in the R5G5 pattern on day 1, and cell migration was observed in the R5G5 and R5G30 patterns on day 5. However, most of the cells did not arrive at the R5G10 and R5G20 patterns, and it was observed that the R5G10 pattern was the most effective on inhibiting migration of the cells. In this case, a cell migration inhibition rate was 98.75%.

In the case of the R5G10 pattern, the cells migrate in the direction of the pattern rather than migrating in the traversing direction of the pattern in a state of being stuck in the pattern with orientation, and thus it may be understood that the R5G10 pattern has the effect on controlling migration of the cells. On the contrary, in the cases of the R5G20 and R5G30 patterns, more surfaces of the nanostructures are exposed and the cells are adhered to the nanostructures surface, and thus it may be understood that the number of cells migrating the pattern in the traversing direction decreases.

Figure 7:
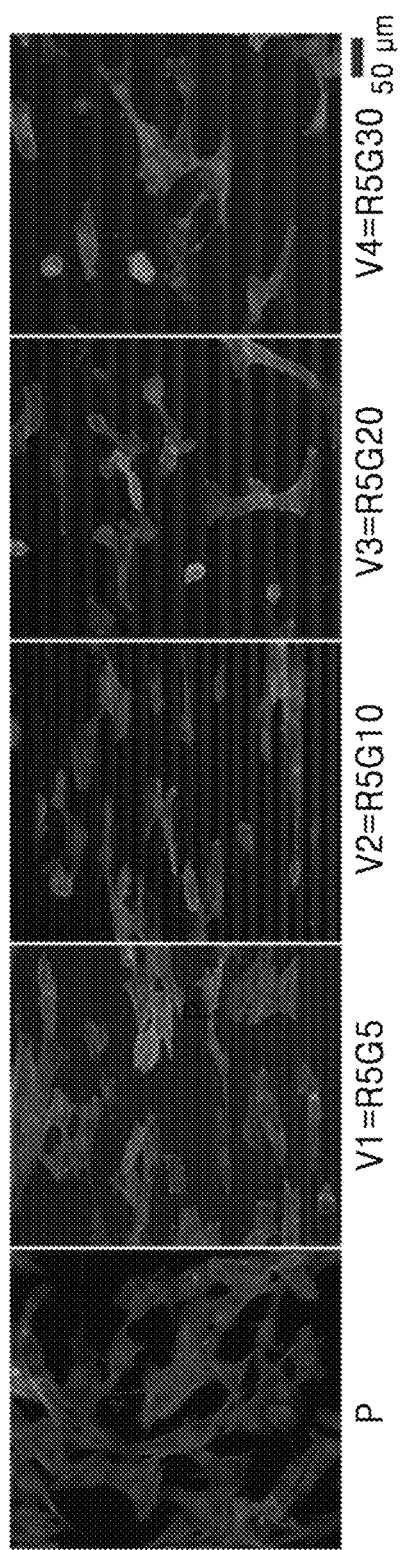
FIG. 7 shows microscope images of cells for identifying cell migration according to widths of grooves among sizes of a pattern according to embodiments of the present invention.

FIG. 7 shows microscope images of cells for identifying cell migration according to widths of grooves among sizes of a pattern according to embodiments of the present invention.

Referring to FIG. 7 illustrating results of experiments on cell migration behavior, P on the left shows migration behavior of a group of cultured cells observed after 6 hours on a plane, i.e., the nanostructure surface (Ra=93 nm) of the grooves 21 and 22 untreated with a laser, and V1 to V4 show cell migration behavior observed after 6 hours according to the width of the groove on the nanostructure surface (Ra=140 nm) of the grooves 21 and 22. In this regard, the widths R1 and R2 of the ridges were set to be equal to 5 μm (R5), and experimental groups, in which the widths G1 and G2 of the grooves (G5 to G30) were changed to 5 μm (V1=R5G5), 10 μm (V2=R5G10), 20 μm (V3=R5G20), and 30 μm (V4=R5G30), respectively, were compared with each other in the same manner as in the experiment of FIG. 6.

When the experimental groups are maintained for a certain period of time, the degree of cell migration along a lengthwise direction of the pattern may be identified. That is, as shown in FIG. 7, when the cells are maintained under the conditions of the experiment for 6 hours, directivity of cell migration may be identified upon comparison with that that before the cell migration. Based on the results of this experiment, the directivity of cell migration is most clearly observed in V2. It is considered that the cells cannot be stretched widely due to a strong influence of the surface roughness of the nanostructure, thereby decreasing the degree of stretching in V3 and V4. Also, referring to FIG. 7, the entire area of the cells on the surface treated with a laser was reduced compared to that of the cells on the surface P untreated with a laser due to the influence of the widths G1 and G2 of the grooves and the nanostructure surface roughness thereon.

Figure 8:
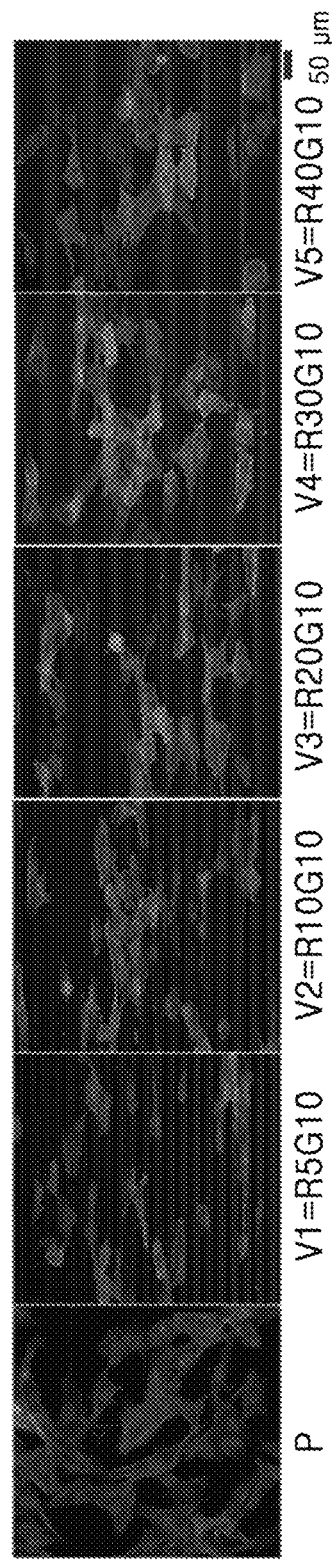
FIG. 8 shows microscope images of cells for identifying cell migration according to sizes of ridges (i.e., intervals between grooves) among sizes of a pattern according to an embodiment of the present invention.

FIG. 8 shows microscope images of cells for identifying cell migration according to sizes of ridges (i.e., interval between grooves) among sizes of a pattern according to an embodiment of the present invention.

Referring to FIG. 8 illustrating results of experiments on cell migration behavior, P on the left shows migration behavior of a group of cultured cells observed after 6 hours on a plane, i.e., the nanostructure surface (Ra=93 nm) of the grooves 21 and 22 untreated with a laser, and V1 to V4 show cell migration behavior observed after 6 hours according to the width of the ridge. In this regard, the widths G1 and G2 of the grooves (i.e., sizes of patterns A and B) having the nanostructure surface having a Ra of 140 nm were set to be equal to 10 μm, and experimental groups, in which the widths R1 and R2 of the ridges (interval between the grooves) were changed to 5 μm (V1=R5G10), 10 μm (V2=R10G10), 20 μm (V3=R20G10), 30 μm (V4=R30G10), and 40 μm (V5=R40G10), respectively, were compared with each other.

When the experimental groups are maintained for a certain period of time, the degree of cell migration along a lengthwise direction of the pattern may be identified. That is, as shown in FIG. 8, when the cells are maintained under the conditions of the experiment for a certain period of time, a direction of cell migration may be identified upon comparison with that that before the cell migration. Based on the results of this experiment, it was confirmed that the cells showed a strong tendency to adhere to the surfaces of the ridges as the widths R1 and R2 of the ridges (i.e., interval between grooves) increased, and thus directivity of the cells deteriorated.

Through the experiments performed according to FIGS. 6 to 8, considering results of the cell migration inhibition rates in the traverse direction of the pattern and directivity of cell migration in the lengthwise direction of the pattern, the widths G1 and G2 of the grooves may be about 10 μm, and the widths R1 and R2 of the ridges may be about 5 μm. In addition, the surface roughness Ra inside the grooves 21 and 22 may be 140 nm in consideration of the directivity of cell migration.

Based on the results of the above-described experiments, it is possible to create an environment affecting the behavior of the cells by adjusting the shapes of the grooves and ridges of the pattern and the surface roughness thereof. The environment may basically include delaying or the migration and proliferation of cells on the optic portion 110 but may further include promoting migration of cells, which migrate from the haptic portion 120 to the optic portion 110, quickly back to the haptic portion 120 or the outer perimeter portion of the optic portion 110. Therefore, the embodiments of the present invention may selectively employ the structures of the patterns A and B indicating different migration speeds of cells according to the section in which the cells are located, thereby controlling the migration of the cells.

In the embodiment of FIG. 1, the patterns A and B may be provided at a position in the vicinity of the optic portion 110 including the outer perimeter portion of the optic portion 110 (position space apart from the center of the optic portion 110) and the haptic portion 120, i.e., a position spaced apart from the optic portion 110.

As described above, the patterns A and B may be provided in different forms to accomplish the above object. These embodiments will be described below with reference to FIGS. 9A and 9B.

Figure 9A:
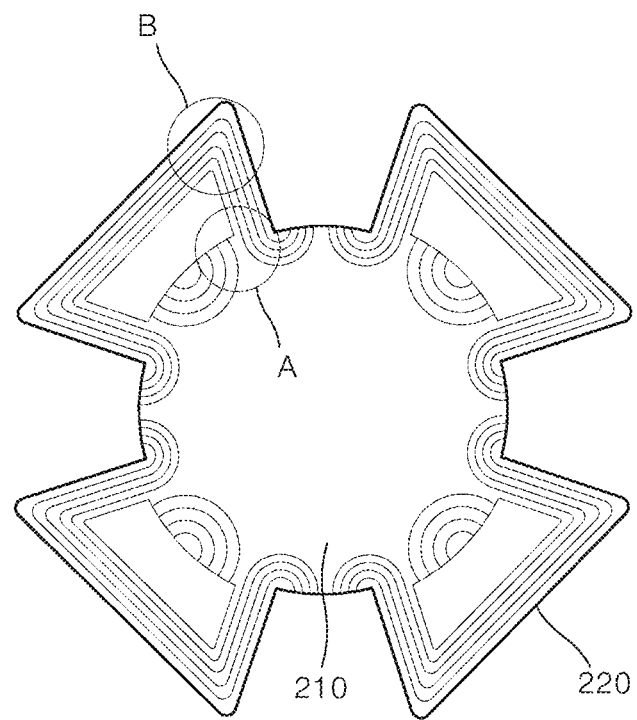
FIGS. 9A and 9B are diagrams exemplarily illustrating patterns formed on intraocular lenses according to another embodiment of the present invention.

FIG. 9A is a diagram exemplarily illustrating patterns A and B formed on intraocular lenses 100 according to another embodiment of the present invention.

Referring to FIG. 9A, a first pattern A may be formed such that the width G1 of the groove is smaller than a width G2 of the groove of a second pattern B. For example, the width R1 of the ridge may be 5 μm, and the width G1 of the groove may be in the range of 10 μm to 30 μm. In the present embodiment, the first pattern A may be formed to guide cells, which migrate from the haptic portion 220 to the optic portion 210, to migrate in a direction farther away from the optic portion 210. The second pattern B may have a wider width G2 of the groove than that of the first pattern A to reduce the mobility of the cells. For example, the width of the ridge 12 may be 5 μm, and the width of the groove 22 may be 30 μm or more.

In addition, the second pattern B formed on the haptic portion 220 may extend on the same line to the optic portion 210, but the first pattern A formed on the optic portion 210 may not be connected to the haptic portion 220 but independently formed in a closed curve shape. The closed curve shape may be formed to be connected from the front surface to the rear surface through the side surface based on the direction in which light passes through the optic portion 210.

That is, the structures of the patterns A and B may decrease a migration speed of cells toward the center of the optic portion 210 and increase a migration speed of cells already adjacent to the optic portion 210 in a direction away from the haptic portion 220 or the optic portion 210 to be higher than the migration speed of cells toward the center of the optic portion 210.

Figure 9B:
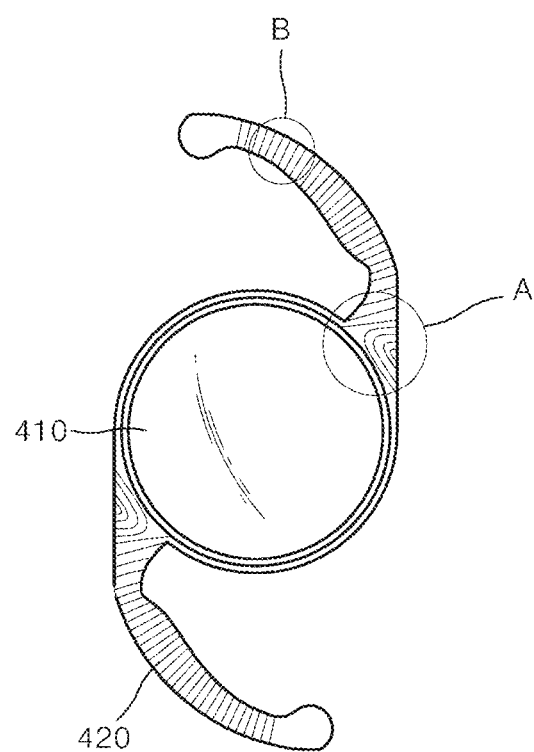

Referring to FIG. 9B, the first pattern A may be formed such that the width G1 of the groove is smaller than the width G2 of the second pattern B. For example, the width R1 of the ridge may be 5 μm, and the width G1 of the groove may be in the range of 10 μm to 30 μm. In the present embodiment, the first pattern A may be formed to guide the cells migrating from a haptic portion 420 to an optic portion 410 in a direction farther away from the optic portion 410.

The second pattern B may be formed such that the width G of the groove is greater than that of the first pattern A to reduce the mobility of the cells. For example, the width of the ridge 12 may be 5 μm, and the width of the groove 22 may be 30 μm or more.

In addition, the patterns A and B formed on the haptic portion 420 may extend on the same line to the optic portion 410, but the first pattern A formed on the optic portion 410 may not be connected to the haptic portion 420 but independently formed in a closed curve shape. The closed curve shape may be formed to be connected from the front surface to the rear surface through the side surface based on the direction in which light passes through the optic portion 410.

That is, the patterns A and B may decrease a migration speed of cells toward the center of the optic portion 410 and increase a migration speed of cells already adjacent to the optic portion 410 in a direction away from the haptic portion 420 or the optic portion 410 to be higher than the migration speed of cells toward the center of the optic portion 410.

Figure 10A:
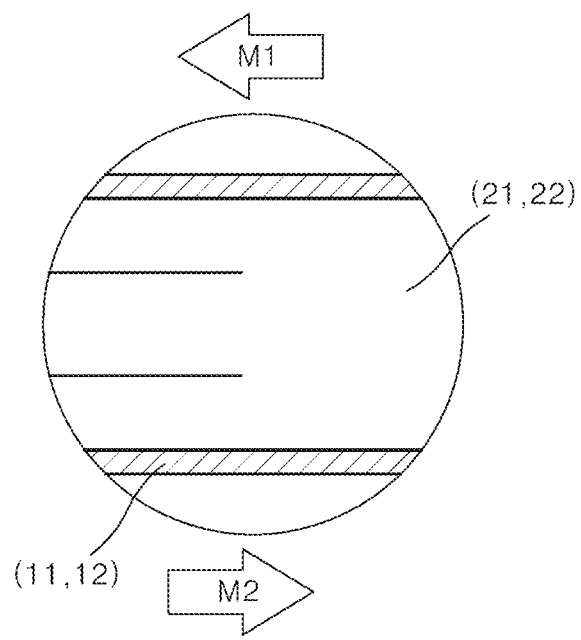
FIGS. 10A to 10C are diagrams illustrating different positions and shapes of boundary portions formed according to embodiments of the present invention.
Figure 10B:
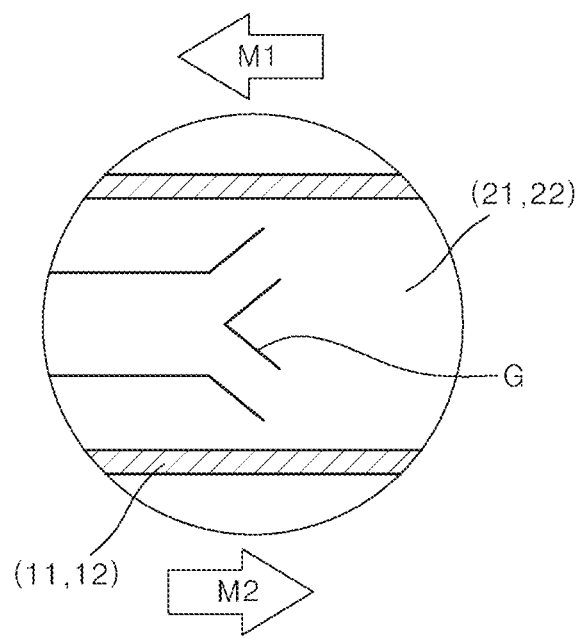
Figure 10C:
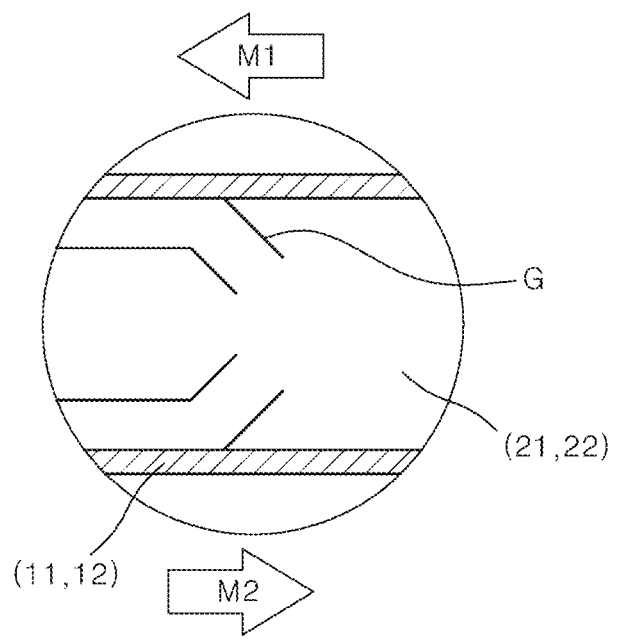

FIGS. 10A to 10C are diagrams illustrating different positions and shapes of boundary portions G formed according to embodiments of the present invention.

Referring to FIG. 10A, a structure that narrows in a cell migration direction M1 from the front side to the rear side may be formed. Specifically, with respect to the entire width, a cell migration path is formed such that a cross-sectional area through which the cells migrate is reduced to ½ or ⅓, and thus a migration speed of the cells may be decreased. Such a structure may be included in a section in which the above-described first pattern A and second pattern B are continuously formed. In this regard, a portion having a narrower cross-sectional area through which cells pass corresponds to the first pattern A, and a portion having a wider cross-sectional area through which cells pass corresponds to the second pattern B. Unlike those described above, a migration direction may also be an opposite migration direction M2.

In the case of the opposite migration direction, this structure may be applied to a section for increasing the migration speed, which may be formed the boundary where cells migrate from the optic portions 110, 210, 310, and 410 to the haptic portion 120, 220, 320, and 420 or any point on the haptic portions 120, 220, 320, and 420. The point may be a point at which the second pattern B is formed.

Referring to FIG. 10B, the boundary portion G may be formed while decreasing the cross-sectional area through which the cells pass. Specifically, the boundary portion G may be configured to inhibit the migration of cells in one direction M1 and change the direction of the cells in the other direction M2 opposite to M1. The present embodiment also corresponds to the case where the cross-sectional area through which cells pass becomes narrower on the rear side and wider on the front side with respect to a traveling direction of cells. It is to be noted that the narrower portion may be the first pattern A, and the wider portion may be the second pattern B. The structure of the boundary portion G may also function as the structure for inhibiting the migration when cells migrate along the migration direction M1.

As a similar structure, referring to FIG. 10C, the cross-sectional area through which cell migrate may be reduced to ⅓ at the rear side in the cell migration direction M1. The boundary portion G may obliquely be formed with respect to the migration direction M1 of the cells at a starting point of the point where the cross-sectional area through which cells pass is reduced. The boundary portion G may obliquely extend toward the front side of the migration direction from the side portions of the grooves 21 and 22, and migration of the cells may be inhibited or delayed by the boundary portion G during the migration due to the structure. Unlike the case described above, in the opposite migration direction M2, the boundary portion G may serve to prevent cells from migrating in the reverse direction.

In the case of the opposite migration direction M2, it may be applied to a section for increasing the migration speed, which may be formed the boundary that migrates from the optic portions 110, 210, 310, and 410 to the haptic portion 120, 220, 320, and 420 or any points on the haptic portions 120, 220, 320, and 420. The point may be a point at which the second pattern B is formed.

Figure 11:
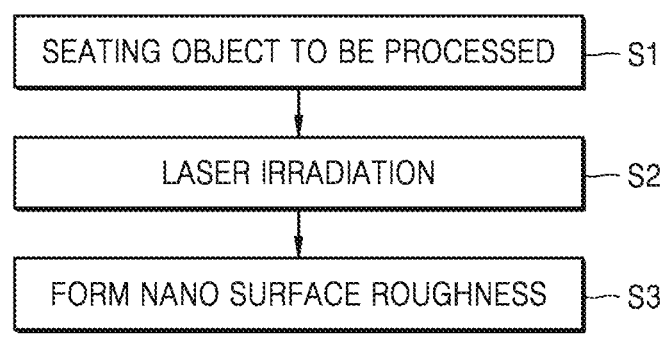
FIG. 11 is a flowchart illustrating a method of manufacturing an intraocular lens according to an embodiment of the present invention.

FIG. 11 is a flowchart illustrating a method of manufacturing an intraocular lens according to an embodiment of the present invention.

The above-described intraocular lenses 100, 300, and 500 may include grooves and ridges with nano-sized surface roughness on surfaces thereof formed by seating an object to be processed (S1) and sequentially performing irradiation of laser beams (S2). The object to be processed may be the intraocular lenses 100, 300, and 500 in a state before a predetermined pattern is formed. The object to be processed may include an optic portion 110, 210, or 410 having a circular shape in one portion thereof and at least one haptic portion 120, 220, or 420 extending from an outer perimeter of the optic portion 110, 210, or 410. The object to be processed is seated on a seating portion (not shown), and the haptic portion 120, 220, or 420 and the optic portion 110, 210, or 410 may be irradiated with laser beams. The grooves and ridges of the pattern formed by the laser beams and nano-sized surface roughness thereof may control behavior of cells.

A structure having a nano-sized surface roughness may be formed on the predetermined pattern formed by the laser beams, and the surface roughness of each of the grooves included in the predetermined pattern may be adjusted to inhibit and control migration of cells.

The preset pattern may be formed such that a width of a groove of the first pattern A formed on the optic portion 110, 210, or 410 is smaller than a width of a groove of the second pattern formed on at least one portion of the haptic portion 120, 220, or 420. The preset pattern may be formed to guide the cells to migrate toward the haptic portion 120, 220, or 420 or the outer perimeter of the optic portion 110, 210, or 410 such that the cells migrate farther away from the center of the optic portion 110, 210, or 410.

According to an embodiment of the present invention as described above, eye diseases such as after cataract may be prevented by controlling the behavior of cells passing through a particular pattern having a predetermined width and the like formed on the intraocular lens.

According to an embodiment of the present invention, the behavior of cells on the intraocular lens may be controlled by forming the particular pattern having a predetermined width and the like and adjusting the nano-sized surface structure formed on the pattern.

According to an embodiment of the present invention, migration of cells may be guided in one direction by forming a boundary portion that reduces the mobility of the cells in the pattern formed on the intraocular lens.

While one or more embodiments of the present invention have been described with reference to the drawings, it will be understood by those of ordinary skill in the art that various changes in form and details may be made therein without departing from the spirit and scope of the present invention as defined by the following claims.

What is claimed is:

1. An intraocular lens comprising:
an optic portion; and
a haptic portion extending from the optic portion,
wherein a pattern having ridges and grooves is formed on at least one of the optic portion and the haptic portion, and
each of the grooves has a nanostructure roughness,
wherein a nanostructure formed on a surface of each of the grooves provides the nanostructure roughness and delays or inhibits migration of cells, and
wherein the surface of the groove has an average roughness Ra of 93 nm to 256 nm by the nanostructure,
wherein each of the grooves comprises a boundary portion,
wherein the boundary portion obliquely extends inward from side walls of the groove to guide a migration direction of cells by narrowing a cross-sectional area through which cells pass in a forward direction of cell migration and blocking the cell migration in a backward direction.

2. The intraocular lens of claim 1, wherein the ridges, the grooves, or both of the ridges and grooves comprise at least one ridge and/or groove having a different width.

3. The intraocular lens of claim 1, wherein the grooves are formed to have a width of 10 μm.

4. The intraocular lens of claim 1, wherein the ridges are formed to have a width of 5 μm.

5. The intraocular lens of claim 1, wherein a ratio between a width of each ridge and a width of each groove is in the range of 1:2 to 1:8.

6. The intraocular lens of claim 1, wherein the pattern is formed over the haptic portion and the optic portion,
the ridges are formed to have a width of 5 μm and the grooves are formed to have different widths according to sections, and
a width of a groove formed on the haptic portion is greater than a width of a groove formed on the optic portion.

7. The intraocular lens of claim 1, wherein the pattern is formed over front and rear surfaces of the optic portion and front and rear surfaces of the haptic portion.

8. The intraocular lens of claim 7, wherein the pattern is continuously formed over the front and rear surfaces via a side surface.

9. The intraocular lens of claim 1, wherein the pattern is formed on at least one of the front and rear surfaces of at least one of the optic portion and the haptic portion.

10. The intraocular lens of claim 1, wherein the boundary portion comprises a plurality of cell migration paths formed within a width of the groove to change a migration speed of the cells.

11. An intraocular lens comprising:
an optic portion; and
a haptic portion extending from the optic portion,
wherein a pattern having ridges and grooves is formed on at least one of the optic portion and the haptic portion,
wherein each of the grooves has a nanostructure roughness,
wherein a nanostructure formed on a surface of each of the grooves provides the nanostructure roughness and delays or inhibits migration of cells,
wherein the boundary portion is formed to protrude upward from the bottom surface of the groove and obliquely extend to bypass and block migration of cells in a forward direction where the cells move and enlarge a cross-sectional area through which the cells pass in a backward direction,
wherein the surface of the groove has an average roughness Ra of 93 nm to 256 nm by the nanostructure.

* * * * *